United States Patent [19]

Ammermann et al.

[11] 4,319,911

[45] Mar. 16, 1982

[54] TRIAZOLYL DERIVATIVES, THEIR MANUFACTURE, AND AGENTS CONTAINING THEM FOR INFLUENCING PLANT GROWTH

[75] Inventors: Eberhard Ammermann, Ludwigshafen; Costin Rentzea, Heidelberg; Johann Jung, Limburgerhof, all of Fed. Rep. of Germany

[73] Assignee: BASF Aktiengesellschaft, Fed. Rep. of Germany

[21] Appl. No.: 143,475

[22] Filed: Apr. 24, 1980

[51] Int. Cl.³ .................... A01N 43/64; C07D 249/08
[52] U.S. Cl. ........................................ 71/76; 71/92; 71/78; 548/101; 548/262
[58] Field of Search .............. 548/262, 101; 71/92, 71/76

[56] References Cited

U.S. PATENT DOCUMENTS 4,113,465  9/1978  Shephard et al. ............... 548/341

FOREIGN PATENT DOCUMENTS

| 940 | 3/1979 | European Pat. Off. | 548/262 |
| 10287 | 4/1980 | European Pat. Off. | 548/262 |
| 2634511 | 2/1978 | Fed. Rep. of Germany | 548/262 |
| 2650831 | 5/1978 | Fed. Rep. of Germany | 548/262 |
| 2739352 | 3/1979 | Fed. Rep. of Germany | 548/262 |

OTHER PUBLICATIONS

Tolbert, J. Biol. Chem., vol. 235, pp. 475–479 (1960).

*Primary Examiner*—Alton D. Rollins
*Attorney, Agent, or Firm*—Keil & Witherspoon

[57] ABSTRACT

Triazolyl derivatives of the formula

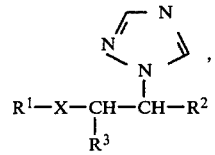

where $R^1$ and $R^2$ are identical or different and each denotes alkyl of from 1 to 6 carbon atoms, naphthyl, unsubstituted phenyl or phenyl substituted by fluoro, chloro, bromo, alkyl or alkoxy of from 1 to 4 carbon atoms, $R^3$ denotes alkyl of from 1 to 4 carbon atoms, unsubstituted benzyl, benzyl substituted by fluoro, chloro, bromo or alkyl of from 1 to 4 carbon atoms, $R^3$ further denotes unsubstituted phenyl, or phenyl substituted by fluoro, chloro, bromo or alkyl of from 1 to 4 carbon atoms, and X denotes C=O or H—C—OR⁴, $R^4$ denoting hydrogen, alkyl of from 1 to 4 carbon atoms, alkenyl of from 1 to 4 carbon atoms, unsubstituted or chloro- or bromo-substituted benzyl, CO—R⁵ or CO—NHR⁵, $R^5$ denoting alkyl of from 1 to 4 carbon atoms, unsubstituted phenyl or phenyl substituted by chloro, bromo or alkyl of from 1 to 4 carbon atoms, the salts and metal complexes thereof, processes for their manufacture, and their use for influencing plant growth.

3 Claims, No Drawings

TRIAZOLYL DERIVATIVES, THEIR MANUFACTURE, AND AGENTS CONTAINING THEM FOR INFLUENCING PLANT GROWTH

The present invention relates to novel triazolyl derivatives, processes for their manufacture, agents for regulating plant growth containing these compounds, and processes for regulating plant growth with these compounds.

The use of 2-chloroethyltrimethylammonium chloride (chlorocholine chloride, CCC) for influencing plant growth has been disclosed (J. Biol. Chem., 235, 475, 1960). With its help, stem length may be reduced in some cereals and vegetative growth inhibited in some other crop plants. However, the action of this compound, particularly at low application rates, is not always satisfactory and does not meet the requirements of practise.

It has also been disclosed (German Laid-Open Application DE-OS No. 2,650,831) to use 1-(4'-bromophenyl)-1-allyloxy-2-(1'',2'',4''-triazol-1''-yl)-ethane for regulating growth in rape, wheat, oats, rye and barley. However, its action, especially at low application rates, is not always satisfactory.

Further, it has been disclosed (German Laid-Open Application DE-OS No. 2,739,352) to use 3,3-dimethyl-2-(1,2,4-triazol-1-yl)-1-(4-chlorobenzoyl)-butane for influencing plant growth.

We have now found that compounds of the formula

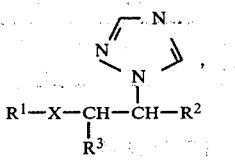

where $R^1$ and $R^2$ are identical of different and each denotes alkyl of from 1 to 6 carbon atoms, naphthyl, unsubstituted phenyl or phenyl substituted by fluoro, chloro, bromo, alkyl or alkoxy of from 1 to 4 carbon atoms, $R^3$ denotes alkyl of from 1 to 4 carbon atoms, unsubstituted benzyl, benzyl substituted by fluoro, chloro, bromo or alkyl of from 1 to 4 carbon atoms, $R^3$ further denotes unsubstituted phenyl, or phenyl substituted by fluoro, chloro, bromo or alkyl of from 1 to 4 carbon atoms, and X denotes C=O or H—C—OR$^4$, R$^4$ denoting hydrogen, alkyl of from 1 to 4 carbon atoms, alkenyl of from 1 to 4 carbon atoms, unsubstituted or chloro- or bromo-substituted benzyl, CO—R$^5$ or CO—NHR$^5$, R$^5$ denoting alkyl of from 1 to 4 carbon atoms, unsubstituted phenyl or phenyl substituted by chloro, bromo or alkyl of from 1 to 4 carbon atoms, and the salts and metal complexes thereof, are excellently suited for influencing plant growth and are very well tolerated by crop plants.

The new compounds of the formula I have 2 or 3 asymmetric centers. From the diastereoisomeric mixtures which synthesis usually yields it is possible to obtain, by conventional methods, uniform diastereoisomeric pairs or uniform enantiomorphs. The present invention also relates to these. Not only the uniform diastereoisomers or enantiomorphs but also the mixtures thereof obtained in synthesis may be used as agents for influencing plant growth. It is preferred to use the mixtures.

We have further found that triazolyl derivatives of the formula I may be produced by (a) reacting 1,2,4-triazole with α,β-unsaturated ketones of the formula

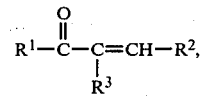

where $R^1$, $R^2$ and $R^3$ have the above meanings, in the presence or absence of a solvent or diluent and in the presence or absence of a basic catalyst.

Some of the α,β-unsaturated ketones of the formula II are known, e.g., 1,2,3-triphenylprop-2-en-1-one, a favorable synthesis route to which is disclosed in German Laid-Open Application DE-OS No. 2,659,293. Corresponding α,β-unsaturated ketones of the formula II may be prepared analogously, or by the conventional methods for specific aldol condensation (see, for example, T. Mukaiyama, K. Banno and K. Narasaka, J. Am. Chem. Soc., 96, 7503, 1974).

The reaction of α,β-unsaturated ketones with 1,2,4-triazole by the above process to give the β-triazolyl ketones of the formula

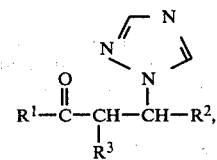

where $R^1$, $R^2$ and $R^3$ have the above meanings, is advantageously carried out without a diluent or in an indifferent diluent, such as methanol, ethanol, isopropanol, tetrahydrofuran, dioxane, toluene, acetonitrile and dimethylformamide, at from 0° to 100° C., preferably from 20° to 60° C.

It is advantageous to add a basic catalyst such as, for example, sodium hydroxide, potassium hydroxide, triethylamine or N,N-dimethylcyclohexylamine to the reaction mixture.

We have further found that triazolyl derivatives of the formula I are also obtained by (b) catalytically reducing β-triazolyl ketones of the formula III with hydrogen or hydrides to give γ-triazolyl alcohols of the formula

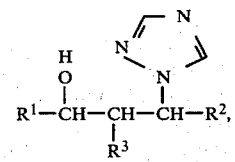

where $R^1$, $R^2$ and $R^3$ have the above meanings, in the presence or absence of a solvent or diluent, and if desired (c) reacting γ-triazolyl alcohols of the formula IV with (α) an alkylating agent of the formula

   V

Hal denoting chlorine, bromine or iodine and $R^4$ having the above meanings with the exception of hydrogen;

(β) an acid halide of the formula $$Hal-\overset{O}{\underset{\|}{C}}-R^5, \quad VI$$

Hal denoting chlorine or bromine and $R^5$ having the above meanings; or (γ) an isocyanate of the formula $$O=C=N-R^5 \quad VII$$

$R^5$ having the above meanings, reactions α, β and γ taking place in the presence or absence of a solvent or diluent, at from 10° to 100° C., in the presence or absence of inorganic or organic bases, and in the presence or absence of a reaction accelerator.

If desired, the compounds obtained by processes a, b and c are reacted with acids or metal salts.

Suitable solvents or diluents for process b are for example water, methanol, ethanol, diethyl ether, tetrahydrofuran, dioxane and toluene.

Examples of hydrides used as reducing agents are sodium borohydride and lithium aluminum hydride.

Platinum or palladium catalysts on inert carriers are used for catalytic hydrogenation, which is carried out at pressures of from 2 to 50 bars until no more hydrogen is absorbed.

For the processes given under c, suitable solvents or diluents are diethyl ether, tetrahydrofuran, dioxane, cyclohexane, methylene chloride, chloroform, toluene and dimethylformamide.

Examples of inorganic or organic bases are alkali metal and alkaline earth metal hydroxides, such as sodium hydroxide, potassium hydroxide and calcium hydroxide; alkali metal hydrides, such as sodium hydride; alkali metal and alkaline earth metal alcoholates, such as sodium ethylate, magnesium methylate and sodium isopropylate; tertiary amines, such as trimethylamine, triethylamine, N,N-dimethylaniline, N,N-dicyclohexylamine and N-methylpiperidine; and pyridine.

It is also possible to convert the γ-triazolyl alcohols in a first reaction into their alcoholate salts with suitable bases, e.g., an alkali metal hydride, such as sodium hydride, or an alkali metal or alkaline earth metal alcoholate, such as sodium methylate, and then to react them as alcoholate salts.

Preferred reaction accelerators for the processes given under c are metal halides, such as potassium iodide, crown ethers, quaternary ammonium compounds, such as tetrabutylammonium iodide, or combinations of these accelerators.

The compounds of the formula I thus obtained are isolated by conventional methods. Generally, they need no further purification, but they may be further purified by conventional methods, such as recrystallization, extraction, distillation or chromatography.

The new active ingredients of the formula I may also be used in the form of their salts, especially those tolerated by crop plants, such as acid addition salts, e.g., hydrochlorides, hydroxalates or hydronitrates.

If desired, the triazolyl derivatives of the formula I may also be converted by conventional processes into metal complexes, particularly those tolerated by crop plants. Such metal complexes are obtained for example by reaction of a triazolyl derivative of the formula I with a metal salt, such as a salt of cobalt, iron, nickel, copper, zinc or manganese, e.g., cobalt chloride, iron-(II) sulfate, nickel nitrate, copper(II) sulfate, zinc chloride, copper(II) chloride or manganese(II) sulfate.

The preparation of the new compounds is illustrated in the following examples.

EXAMPLE 1

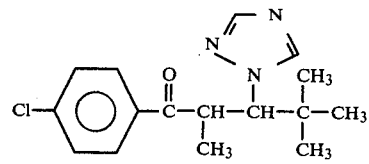

(No. 1)

31 g of 1-(4'-chlorophenyl)-2,4,4-trimethylpent-2-en-1-one in 250 ml of ethanol is stirred for 4 days at 60° C. with 27 g of 1,2,4-triazole and 0.2 g of potassium hydroxide. The reaction mixture is then concentrated, taken up in methylene chloride and washed four times with water. The organic phase is dried, concentrated and separated on silica gel using cyclohexane containing from 1 to 50% ethyl acetate. There is thus obtained 12 g of 4-chlorophenyl-(3'-(1'',2'',4''-triazol-1''-yl)-4',4'-dimethylpent-2'-yl)-ketone as a pale yellow oil. ($n_D^{20}$: 1.5172)

|        | C    | H   | N    | Cl   |
|--------|------|-----|------|------|
| calc.: | 62.8 | 6.6 | 13.7 | 11.6 |
| found: | 62.7 | 6.2 | 13.2 | 11.2 |

EXAMPLE 2

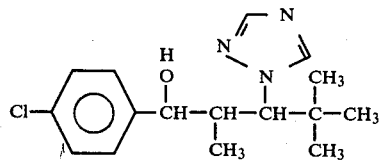

(No. 2)

14 g of 4-chlorophenyl-(3'-(1'',2'',4''-triazol-1''-yl)-4',4'-dimethylpent-2'-yl)-ketone is dissolved in 250 ml of absolute methanol; at 0° C., 2.75 g of sodium borohydride is then added in portions. The mixture is stirred overnight, acidified with concentrated hydrochloric acid, then neutralized with ammonia and concentrated to dryness. The residue is taken up in methylene chloride and washed three times with water. After the organic phase has been dried and concentrated, there remains 11 g of 1-(4'-chlorophenyl)-2,4,4-trimethyl-3-(1'',2'',4''-triazol-1''-yl)-pent-1-yl alcohol as a clear oil ($n_D^{20}$: 1.5350).

|        | C    | H   | N    | Cl   |
|--------|------|-----|------|------|
| calc.: | 62.6 | 6.9 | 13.7 | 11.5 |
| found: | 62.1 | 6.6 | 13.3 | 10.9 |

EXAMPLE 3

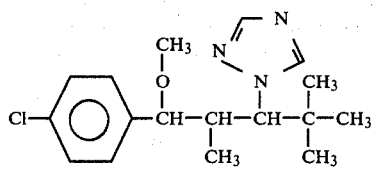
(No. 3)

1.7 g of sodium hydride is suspended in 150 ml of absolute tetrahydrofuran (THF); at 40° C., a solution of 10 g of 1-(4'-chlorophenyl)-2,4,4-trimethyl-3-(1", 2",4"-triazol-1"-yl)-pentyl-1-alcohol in 50 ml of absolute THF is slowly added. After the mixture has been stirred for 2 hours at 50° C., it is cooled to room temperature, and a solution of 7.1 g of methyl iodide in 10 ml of absolute THF is dripped in. After the mixture has been stirred overnight, the excess sodium hydride is decomposed with water. The reaction mixture is neutralized with sulfuric acid and concentrated. The residue is taken up in water and extracted twice with methylene chloride. The solution is dried and the solvent evaporated off. There remains 9 g of methyl-(1-(4'-chlorophenyl)-2,4,4-trimethyl-3-(1",2",4"-triazol-1"-yl)-pent-1-yl)-ether as a colorless oil.

|        | C    | H   | N    | Cl   |
|--------|------|-----|------|------|
| calc.: | 63.4 | 7.5 | 13.0 | 11.0 |
| found: | 63.7 | 7.9 | 12.6 | 10.7 |

EXAMPLE 4

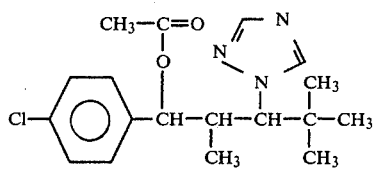
(No. 4)

15 g of 1-(4'-chlorophenyl)-2,4,4-trimethyl-3-(1",2",4"-triazol-1"-yl)-pent-1-yl alcohol, 1 g of imidazole and 8.5 ml of triethylamine are dissolved in 200 ml of absolute THF. While stirring, 5.6 ml of acetic anhydride is dripped in and the mixture is then refluxed, with stirring, for 2 hours. After the mixture has cooled it is concentrated, and the residue is taken up in methylene chloride and washed three times with water. The organic phase is dried, concentrated, and purified on silica gel using methylene chloride as eluant. There is thus obtained 8 g of acetic acid-1-(4'-chlorophenyl)-2,4,4-trimethyl-3-(1",2",4"-triazol-1"-yl)-pent-1-yl ester as a colorless oil ($n_D^{20}$: 1.5071).

|        | C    | H   | N    | Cl   |
|--------|------|-----|------|------|
| calc.: | 61.9 | 6.6 | 12.0 | 10.1 |
| found: | 61.7 | 7.0 | 11.8 | 9.8  |

The following triazolyl derivatives of the formula I, which were identified by infrared and nmr spectroscopy and elemental analysis, were prepared analogously:

| No. | R¹         | X              | R²              | R³          | m.p./$n_D^{20}$         |
|-----|------------|----------------|-----------------|-------------|-------------------------|
| 5   | CH₃—       | C=O            | 4-Cl—C₆H₄—      | C₆H₅        |                         |
| 6   | CH₃—       | C=O            | C₆H₅—           | C₆H₅—       | 184–187                 |
| 7   | CH₃—       | C=O            | C₆H₅—           | 4-Cl—C₆H₄—  | as hydrochloride 109–113 |
| 8   | C₆H₅       | HCOH           | C₆H₅—           | CH₃—        | 136–138                 |
| 9   | C₆H₅—      | C=O            | 2-Cl—C₆H₄—      | CH₃—        | 147–150                 |
| 10  | C₆H₅—      | C=O            | C₆H₅—           | CH₃—        | 111–114                 |
| 11  | C₆H₅—      | C=O            | (benzodioxol)   | CH₃—        | 179–181                 |
| 12  | C₆H₅—      | C=O            | n-C₃H₇—         | CH₃—        | oil                     |
| 13  | C₆H₅—      | C=O            | tert.-C₄H₉—     | CH₃—        | oil                     |
| 14  | 4-F—C₆H₄—  | C=O            | tert.-C₄H₉—     | CH₃—        | 1.518                   |
| 15  | C₆H₅—      | C=O            | tert.-C₄H₉—     | n-C₄H₉—     | 1.5022                  |
| 16  | C₆H₅—      | C=O            | i-C₃H₇—         | —CH₃        | oil                     |
| 17  | 4-Cl—C₆H₄— | C=O            | i-C₃H₇—         | —CH₃        | oil                     |
| 18  | 4-Cl—C₆H₄— | C=O            | n-C₃H₇—         | —CH₃        | oil                     |
| 19  | 4-Cl—C₆H₄— | HC—OCH₂CH₃     | tert.-C₄H₉—     | —CH₃        |                         |
| 20  | 4-Cl—C₆H₄— | HC—OCOCH₂—CH₃  | tert.-C₄H₉—     | —CH₃        | 1.5009                  |
| 21  | C₆H₅—      | C=O            | cyclo-C₆H₁₁—    | CH₃—        |                         |
| 22  | 4-Cl—C₆H₄— | C=O            | cyclo-C₆H₁₁—    | CH₃—        | resin                   |
| 23  | C₆H₅—      | C=O            | C₆H₅—           | C₆H₅—       |                         |
| 24  | C₆H₅—      | HCOH           | C₆H₅—           | C₆H₅—       |                         |
| 25  | C₆H₅—      | HCO(CO)NHCH₃   | C₆H₅—           | C₆H₅—       |                         |
| 26  | C₆H₅       | C=O            | 4-Cl—C₆H₅—      | C₆H₅—       |                         |
| 27  | 4-Cl—C₆H₄— | HCOCH₂—CH=CH₂  | tert.-C₄H₉—     | CH₃—        |                         |
| 28  | 4-Cl—C₆H₄— | HCOCH₂C₆H₅     | tert.-C₄H₉—     | CH₃—        |                         |
| 29  | 4-Cl—C₆H₄— | HCO(CO)C₆H₅    | tert.-C₄H₉—     | CH₃—        |                         |
| 30  | 4-Cl—C₆H₄— | HCO(CO)NHC₆H₅  | tert.-C₄H₉—     | CH₃—        |                         |

The new compounds may influence practically all development stages of a plant in different ways. They are therefore used as plant growth regulators.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) climatic factors (sunshine duration, average temperature, precipitate);

(e) soil conditions (including fertilization);

(f) the formulation or application form of the active ingredient; and (g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportgrounds, fruit orchards, lawns and airfields, thus reducing expensive and time-consuming mowing.

A further feature of economic interest is the increase in the rigor of crops which tend to lodge, such as cereals, Indian corn and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of interest when it is desired to inhibit, for instance in tobacco plants, the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various diseases, especially fungus diseases. The inhibition of vegetative growth also makes closer planting possible in numerous crops, which means an increase in yield based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also responsible for a chemically induced, readily controllable defoliation of plants.

The action of the compounds according to the invention is superior to that of prior art growth regulators. This action is manifested not only in monocotyledon crops, e.g., cereals such as wheat, barley, rye, oats and rice or Indian corn, but also in dicotyledons (e.g., sunflowers, tomatoes, soybeans, grapes, cotton and, particularly, rape) and various ornamentals such as chrysanthemums, poinsettias and hibiscus.

The compounds according to the invention may be applied to the crop either by treating the seed, treating the soil, i.e., through the roots, or by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.01 to 12 kg/ha, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95 percent by weight of active ingredient, preferably from 0.5 to 90 percent.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

The agents according to the invention may, in these application forms, also be mixed and applied with other active ingredients, e.g., herbicides, insecticides, other growth regulators, bactericides, fungicides and fertilizers. When mixed with other growth regulators, the spectrum of action is in many cases increased; with a number of these compositions, synergistic effects also occur; i.e., the action of the combination product is greater than the effect of the individual components added together.

The following examples demonstrate the action of the compounds according to the invention as growth regulators; however, further applications as growth regulators are not excluded.

Plastic pots 12.5 cm in diameter were filled with a soil provided with sufficient nutrients, and test plants grown therein. In the preemergence treatment, the substances to be tested were sprayed, as aqueous formulations at various concentrations, onto the surface of the soil on the day the seeds were sown. In the postemergence treatment, the plants were sprayed with aqueous formulations at various concentrations. The growth-regulating action observed was confirmed at the end of the experiment by height measurement. The values obtained were compared with those for untreated plants. The comparative agents employed were the prior art compounds given below.

The individual figures are given in the following tables.

| Comparative agents | |
|---|---|
| CCC | 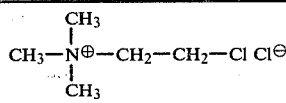 |
| disclosed in German Laid-Open Application DE-OS 2,650,831 A | 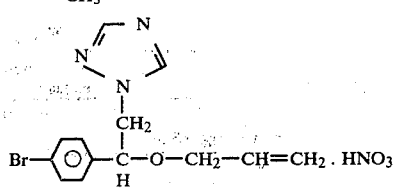 |
| disclosed in German Laid-Open Application DE-OS 2,739,352 B | 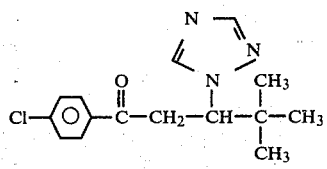 |

TABLE 1

Preemergence treatment - summer wheat "Kolibri"
Duration of expt.: 14 days

| Active ingredient | Concentration mg a.i./vessel | Growth height cm | % |
|---|---|---|---|
| untreated | — | 26.1 | 100 |
| CCC | 3 | 18.5 | 70.9 |
|  | 12 | 17.5 | 67.0 |
| 1 | 3 | 15.5 | 59.4 |
|  | 12 | 11.0 | 42.1 |
| 16 | 3 | 15.0 | 57.5 |
|  | 12 | 8.0 | 30.7 |
| 17 | 3 | 15.0 | 57.5 |

TABLE 1-continued

Preemergence treatment - summer wheat "Kolibri"
Duration of expt.: 14 days

| Active ingredient | Concentration mg a.i./vessel | Growth height cm | % |
|---|---|---|---|
|  | 12 | 10.0 | 38.3 | a.i. = active ingredient

TABLE 2

Postemergence treatment - summer wheat "Kolibri"
Duration of expt.: 14 days

| Active ingredient | Concentration mg a.i./vessel | Growth height cm | % |
|---|---|---|---|
| untreated | — | 26.3 | 100 |
| B | 1.5 | 24.0 | 91.3 |
|  | 6 | 23.5 | 89.4 |
| 1 | 1.5 | 20.5 | 77.9 |
|  | 6 | 20.5 | 77.9 |
| 16 | 1.5 | 22.0 | 83.7 |
|  | 6 | 21.0 | 79.8 |
| 17 | 1.5 | 22.5 | 85.6 |
|  | 6 | 22.0 | 83.7 |

TABLE 3

Preemergence treatment - summer barley "Union"
Duration of expt.: 15 days

| Active ingredient | Concentration mg a.i./vessel | Growth height cm | % |
|---|---|---|---|
| untreated | — | 26.9 | 100 |
| CCC | 3 | 21.5 | 79.9 |
|  | 12 | 19.5 | 72.5 |
| A | 3 | 25.5 | 94.8 |
|  | 12 | 22.0 | 81.8 |
| B | 3 | 23.0 | 85.5 |
|  | 12 | 18.0 | 66.9 |
| 16 | 3 | 21.5 | 79.9 |
|  | 12 | 13.0 | 48.3 |
| 17 | 3 | 21.0 | 78.1 |
|  | 12 | 16.0 | 59.5 |

TABLE 4

Postemergence treatment - summer barley "Union"
Duration of expt.: 15 days

| Active ingredient | Concentration mg a.i./vessel | Growth height cm | % |
|---|---|---|---|
| untreated | — | 27.7 | 100 |

TABLE 4-continued

Postemergence treatment - summer barley "Union"
Duration of expt.: 15 days

| Active ingredient | Concentration mg a.i./vessel | Growth height cm | % |
|---|---|---|---|
| CCC | 1.5 | 26.0 | 93.9 |
|  | 6 | 25.0 | 90.3 |
| A | 1.5 | 27.0 | 97.5 |
|  | 6 | 25.0 | 90.3 |
| B | 1.5 | 27.0 | 97.5 |
|  | 6 | 26.5 | 95.7 |
| 1 | 1.5 | 25.0 | 90.3 |
|  | 6 | 22.0 | 79.4 |

TABLE 5

Preemergence treatment - oats "Flamingkrone"
Duration of expt.: 17 days

| Active ingredient | Concentration mg a.i./vessel | Growth height cm | % |
|---|---|---|---|
| untreated | — | 26.4 | 100 |
| CCC | 3 | 24.5 | 92.8 |
|  | 12 | 23.5 | 89.0 |
| A | 3 | 24.5 | 92.8 |
|  | 12 | 21.0 | 79.6 |
| 16 | 3 | 24.0 | 90.9 |
|  | 12 | 16.0 | 60.6 |
| 17 | 3 | 23.5 | 89.0 |
|  | 12 | 17.0 | 64.4 |

TABLE 6

Postemergence treatment - lawn
Duration of expt.: 63 days

| Active ingredient | Concentration mg a.i./vessel | Growth height cm | % |
|---|---|---|---|
| untreated | — | 10.3 | 100 |
| B | 1.5 | 9.0 | 87.4 |
|  | 6 | 8.0 | 77.7 |
| 1 | 1.5 | 7.0 | 68.0 |
|  | 6 | 5.0 | 48.5 |
| 16 | 1.5 | 9.0 | 87.4 |
|  | 6 | 7.0 | 68.0 |
| 17 | 1.5 | 9.0 | 87.4 |
|  | 6 | 7.0 | 68.0 |

TABLE 7

Postemergence treatment - soybeans "SRF 450"
Duration of expt.: 28 days

| Active ingredient | Concentration mg a.i./vessel | Growth height cm | % |
|---|---|---|---|
| untreated | — | 25.6 | 100 |
| CCC | 1.5 | 24.0 | 93.8 |
|  | 6 | 21.0 | 82.0 |
| A | 1.5 | 25.5 | 99.6 |
|  | 6 | 23.5 | 91.8 |
| B | 1.5 | 25.0 | 97.7 |
|  | 6 | 24.5 | 95.7 |
| 1 | 1.5 | 20.5 | 80.1 |
|  | 6 | 15.0 | 58.6 |

Not only was growth height reduced—the leaves were also more intensely colored. The increased chlorophyll content also indicates an increased rate of photosynthesis; consequently, a higher yield may be expected.

TABLE 8

Postemergence treatment - soybeans "SRF 450"
Duration of expt.: 29 days

| Active ingredient | Concentration mg a.i./vessel | Growth height cm | % |
|---|---|---|---|
| untreated | — | 20.8 | 100 |
| CCC | 1.5 | 20.5 | 98.6 |
|  | 6 | 19.5 | 93.8 |
| B | 1.5 | 20.0 | 96.2 |
|  | 6 | 20.0 | 96.2 |
| 3 | 1.5 | 16.5 | 79.3 |
|  | 6 | 11.5 | 55.3 |

TABLE 9

Postemergence treatment - soybeans "SRF 400"
Duration of expt.: 40 days

| Active ingredient | Concentration mg a.i./vessel | Growth height cm | % |
|---|---|---|---|
| untreated | — | 26.3 | 100 |
| CCC | 1.5 | 25.0 | 95.1 |
|  | 6 | 24.0 | 91.3 |
| B | 1.5 | 24.0 | 91.3 |
|  | 6 | 24.0 | 91.3 |
| 10 | 1.5 | 24.0 | 91.3 |
|  | 6 | 23.5 | 89.4 |
| 11 | 1.5 | 19.5 | 74.1 |
|  | 6 | 19.0 | 72.2 |

TABLE 10

Preemergence treatment - summer rape "Cosa"
Duration of expt.: 22 days

| Active ingredient | Concentration mg a.i./vessel | Growth height cm | % |
|---|---|---|---|
| untreated | — | 21.1 | 100 |
| CCC | 3 | 19.0 | 90.1 |
|  | 12 | 18.5 | 87.7 |
| A | 3 | 16.0 | 75.8 |
|  | 12 | 10.5 | 49.8 |
| B | 3 | 15.5 | 73.5 |
|  | 12 | 11.5 | 54.5 |
| 1 | 3 | 14.0 | 66.4 |
|  | 12 | 7.0 | 33.2 |

TABLE 11

Postemergence treatment - summer rape "Cosa"
Duration of expt.: 21 days

| Active ingredient | Concentration mg a.i./vessel | Growth height cm | % |
|---|---|---|---|
| untreated | — | 21.3 | 100 |
| CCC | 1.5 | 19.5 | 91.6 |
|  | 6 | 19.0 | 89.2 |
| B | 1.5 | 19.5 | 91.6 |
|  | 6 | 18.0 | 84.5 |
| 1 | 1.5 | 15.0 | 70.4 |
|  | 6 | 8.0 | 56.3 |
| 2 | 1.5 | 19.0 | 89.2 |
|  | 6 | 16.5 | 77.5 |
| 14 | 1.5 | 20.0 | 93.9 |
|  | 6 | 15.0 | 70.4 |

EXAMPLE A 90 parts by weight of compound 1 is mixed with 10 parts by weight of N-methyl-α-pyrrolidone. A mixture is obtained which is suitable for application in the form of very fine drops.

EXAMPLE B 20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE C 20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE D 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE E 20 parts by weight of compound 3 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE F 3 parts by weight of compound 3 is intimately mixed with 97 parts by weight of particulate kaolin. A dust is obtained containing 3% by weight of the active ingredient.

EXAMPLE G 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE H 40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE I 20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. A triazolyl derivative selected from the group consisting of:
4-chlorophenyl-[3'-(1'',2'',4''-triazol-1''-yl)-4',4'-dimethylpent-2'-yl]-ketone;
1-(4'-chlorophenyl)-2,4,4-trimethyl-3-[(1'',2'',4''-triazol-1''-yl)-pent-1-yl]-alcohol;
methyl-1-(4''-chlorophenyl)-2,4,4-trimethyl-3-[(1'',2'',4''-triazol-1''-yl)-pent-1-yl]-ether;
1,3-diphenyl-2-methyl-3-[(1'',2'',4''-triazol-1''-yl)-prop-1-yl]-alcohol;
phenyl-[3'(1'',2'',4''-triazol-1''-yl)-3'-α-naphthylprop-2'-yl]-ketone;
4-fluorophenyl-[3'-(1'',2'',4''-triazol-1''-yl)-4',4'-dimethylpent-2'-yl]-ketone;
phenyl-[3'-(1'',2'',4''-triazol-1''-yl)-4'-methylpent-2'-yl]-ketone;
4-chlorophenyl-[3'-(1'',2'',4''-triazol-1''-yl)-4'-methylpent-2'-yl]-ketone;
the acid addition salts thereof; or a complex formed by reacting the triazolyl derivative with a salt of cobalt, iron, nickel, copper, zinc or manganese.

2. A process for reducing the stem length in growing plants, wherein the plants, seed or the soil are treated with a triazolyl derivative selected from the group consisting of:
4-chlorophenyl-[3'-(1'',2'',4''-triazol-1''-yl)-4',4'-dimethylpent-2'-yl]-ketone;
1-(4'-chlorophenyl)-2,4,4-trimethyl-3-[(1'',2'',4''-triazol-1''-yl)-pent-1-yl]-alcohol;
methyl-1-(4'chlorophenyl)-2,4,4-trimethyl-3-[(1'',2'',4''-triazol-1''-yl)-pent-1-yl]-ether;
1,3-diphenyl-2-methyl-3-[(1'',2'',4''-triazol-1''-yl)-prop-1-yl]-alcohol;
phenyl-[3'-(1'',2'',4''-triazol-1''-yl)-3'-α-naphthylprop-2'-yl]-ketone;
4-fluorophenyl-[3'-(1'',2'',4''-triazol-1''-yl)-4',4'-dimethylpent-2'-yl]-ketone;
phenyl-[3'-(1'',2'',4''-triazol-1''-yl)-4'-methylpent-2'-yl]-ketone;
4-chlorophenyl-[3'-(1'',2'',4''-triazol-1''-yl)-4'-methylpent-2'-yl]-ketone;
the acid addition salts thereof; or a complex formed by reacting the triazolyl derivative with a salt of cobalt, iron, nickel, copper, zinc or manganese.

3. A triazolyl derivative selected from the group consisting of 4-chlorophenyl-(3'-(1'',2'',4''-triazol-1''-yl)-4',4'-dimethylpent-2'-yl)-ketone and methyl-(1-(4'-chlorophenyl)-2,4,4-trimethyl-3-(1'',2'',4''-triazol-1''-yl)-pent-1-yl)-ether.

* * * * *

UNITED STATES PATENT AND TRADEMARK OFFICE
CERTIFICATE OF CORRECTION

PATENT NO. : 4,319,911
DATED : March 16, 1982
INVENTOR(S) : E. Ammermann; C. Rentzea; and J. Jung It is certified that error appears in the above—identified patent and that said Letters Patent is hereby corrected as shown below:

On the title page add Item /30/ Foreign Application Priority Data --May 25, 1979, Federal Republic of Germany . . . 2921168--.

Claim 1, Column 14, line 18, "(4"-" should read --(4'- --.

Signed and Sealed this

Tenth Day of August 1982

[SEAL]

Attest:

GERALD J. MOSSINGHOFF

Attesting Officer

Commissioner of Patents and Trademarks